United States Patent [19]

Rupe et al.

[11] 4,092,115
[45] May 30, 1978

[54] METHOD, DEVICE AND TEST REAGENT FOR DETECTING FREE AVAILABLE CHLORINE IN AQUEOUS FLUIDS

[75] Inventors: Chauncey Orvis Rupe, Jerusalem, Israel; Robert Bauer, Bristol, Ind.

[73] Assignee: Miles Laboratories, Inc., Elkhart, Ind.

[21] Appl. No.: 798,750

[22] Filed: May 20, 1977

Related U.S. Application Data

[63] Continuation of Ser. No. 460,022, April 11, 1974, abandoned, which is a continuation-in-part of Ser. No. 12,571, Feb. 19, 1970, abandoned.

[51] Int. Cl.$^2$ .................. G01N 31/22; G01N 33/18
[52] U.S. Cl. .................. 23/230 R; 23/253 TP; 252/408
[58] Field of Search ........... 23/230 R, 230 B, 253 TP; 195/103.5 R; 252/408; 116/114 AM

[56] References Cited

U.S. PATENT DOCUMENTS

| | | | |
|---|---|---|---|
| 2,385,471 | 9/1945 | Scharer | 23/230 B |
| 3,008,879 | 11/1961 | Harvill | 23/253 TP X |
| 3,104,209 | 9/1963 | Scott | 23/253 TP X |
| 3,233,974 | 2/1966 | Bradley | 23/253 TP |

Primary Examiner—Robert M. Reese
Attorney, Agent, or Firm—E. H. Gorman

[57] ABSTRACT

A method, device and test reagent for detecting free available chlorine in aqueous fluids which utilizes as an indicator substance azine compounds of the formula:

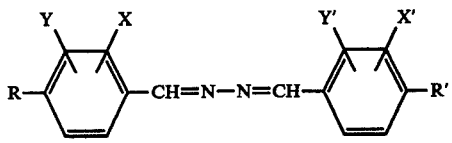

where R and R' are hydroxy or amino substituents and X, X', Y and Y' are hydrogen, hydroxy, methyl or methoxy substituents and may be the same or different. Preferably such test reagents are incorporated with a carrier member or with a wicking device for concentrating the aqueous fluid being tested in the area of the test reagent.

6 Claims, 5 Drawing Figures

METHOD, DEVICE AND TEST REAGENT FOR DETECTING FREE AVAILABLE CHLORINE IN AQUEOUS FLUIDS

CROSS-REFERENCE TO RELATED APPLICATION

This is a continuation of application Ser. No. 460,022, filed Apr. 11, 1974, now abandoned, which was a continuation-in-part of U.S. application Ser. No. 12, 571, filed Feb. 19, 1970, now abandoned.

BACKGROUND OF THE INVENTION

This invention relates to a rapid method, a reagent and a device for detecting free available chlorine in aqueous fluids. More particularly, this invention concerns the use, as an indicator substance, of certain azine compounds which have unexpectedly been found to differentiate between free available chlorine and combined available chlorine in aqueous fluids.

The available chlorine family, which is of particular interest in the bleaching and disinfecting fields, is comprised of the chemicals which, when in aqueous solution, yield solutions of hypochlorous acid. These compounds are further subdivided into those which contain free available chlorine and those which contain combined available chlorine.

Free available chlorine describes chlorine in aqueous solution as hypochlorous acid, hypochlorite ion or, in strong acid solutions, as free chlorine. The use of free available chlorine as a disinfectant for swimming pool water and other water supplies has been popular for some time. Its popularity is due, in part, to its low cost, convenience and effectiveness as an antiseptic agent in relatively low concentrations. It is widely accepted that hypochlorous acid has the ability to diffuse through the cell wall of the bacterial cell and thereby cause the death of the cell. Since the amount of free available chlorine in an aqueous solution relates directly to the disinfecting or sanitizing activity thereof, a test which will rapidly and accurately measure free available chlorine has long been desired. This is particularly true since it is known that major disadvantages of free available chlorine are: (1) in higher than necessary concentrations, it is irritating to the eyes, (2) it has an unpleasant odor and (3) it rapidly dissipates from exposed water, either by escaping as a gas or by reacting with some component in water.

In the interest of adequate swimming pool sanitation and pleasant swimming, it is desirable to maintain the free available chlorine content of swimming pool water somewhere between the lowest effective concentration conducive to good sanitation and the highest concentration that is not irritating to the eyes. This range is fairly narrow, covering a concentration range of frome about 0.4 ppm. to about 2.0 ppm.

Combined available chlorine is mainly associated with organic chloramines which when in aqueous solution release only a small amount of free available chlorine. The balance of the chlorine is in a combined state which is not believed to be effective for disinfecting. Accordingly, systems which measure combined available chlorine together with free available chlorine yield results which are not truly indicative of the level of disinfectant in the solution tested.

In the past, oxidation-reduction indicators have been utilized for detecting chlorine in swimming pool and drinking water. However, it was known that such tests not only detected free available chlorine under ordinary conditions and use, but were also sensitive to combined available chlorine. Since the disinfecting activity of chlorine-containing compounds is due primarily to free available chlorine, it is extremely advantageous that a system for testing aqueous fluids for their bactericidal ingredients detect free available chlorine only, rather than free and combined available chlorine.

Exemplary of the prior art oxidation-reduction indicator systems which are still used to test aqueous fluids for chlorine are those which in the presence of chlorine change from one color to another, from a colored to a colorless material or from a colorless to a colored material. In the past materials such as o-tolidine, dimethyl-p-phenylenediamine (DPD), diphenylamine sulfate, naphthol, napthoflavone, o-toluidine, aniline and the like have been used in systems as chlorine indicators.

One oxidation-reduction indicator system which is used to measure free available chlorine and combined available chlorine is referred to as the orthotolidine-arsenite (OTA) method. In this method total chlorine is measured with orthotolidine (OT), a reading of color intensity being made five minutes after the addition of the OT to the water. Another test is made on a second sample of water by adding sodium arsenite thereto immediately following the addition of OT. It is critical that the sodium arsenite be added within 5 seconds of the first addition of OT, since the former reagent immediately reduces the combined available chlorine (chloramines) and prevents further reaction with OT. This latter test is read for color intensity and thereby gives a reading of free available chlorine in the sample. This test method and other test methods are more fully described in Sconce, J.S., "Chlorine, Its Manufacture, Properties and Uses," pp 475–477, New York, Reinhold Publishing Corporation, 1962. It can be seen from the foregoing that methods for the determination of free available chlorine have been complex and often required critical manipulative steps.

SUMMARY OF THE INVENTION

It has now been found that a highly effective method, test reagent and device for measuring free available chlorine is achieved by the utilization as an indicator substance of an azine compound or a combination of azine compounds. An advantageous test device is prepared by using the azine compound in conjunction with a carrier member which may comprise an impregnated bibulous paper device or an impregnated bibulous paper wicking device as described hereinafter for concentrating in the vicinity of the test reagent the free available chlorine in the aqueous fluid being tested.

DESCRIPTION OF THE PREFERRED EMBODIMENTS

The test reagent of the present invention for detecting free available chlorine comprises, as an indicator substance, one or more azine compounds represented by the formula:

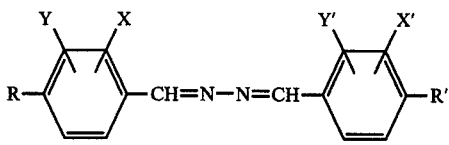

where R and R' are OH or $NH_2$ substituents and X, X', Y and Y' are H, OH, $CH_3$ or $OCH_3$ substituents. Preferably X, X', Y and Y' are meta substituted methoxy groups. Exemplary of the azine type compounds which are useful in the indicator system of the present invention are vanillinazine in which R and R' are OH, X and X' are meta methoxy and Y and Y' are H; syringaldazine in which R and R' are OH and Y, X, Y' and X' are meta methoxy; 2, 4, 6, 2', 4', 6' hexahydroxy benzaldazine; 3, 4, 3', 4' tetrahydroxybenzaldazine; and the like.

The amount of test reagent used is not critical so long as the desired hue and color saturation is achieved in the final product. However, as a general guide about from 0.02 mg. to 0.1 mg. is used in a test device or system for detecting free available chlorine in aqueous fluids.

A particularly advantageous test reagent composition of the present invention involves the use of the above described indicator compounds in combination with a buffer system having a pH of about from 3.5 to 8.5 and preferably about 6.0. The use of such a pH condition has been found to result in a test reagent system having increased sensitivity and color response when contacted with free available chlorine dissolved in aqueous fluids. Test reagent systems using such a buffer have resulted in an increase in color response of about from 25% to 50% of the color response achieved without the buffer. Phosphate buffers have been found to be particularly advantageous for use with the test reagent systems of the present invention. A technical explanation of why such a pH condition results in increased color response is not known at this time.

Another preferable embodiment of the present invention involves the use of a carrier for the test reagent. By using a carrier such as bibulous paper to contain and carry out the test reaction, it has been found that the color stability of the test reagent is significantly improved.

The test reagent of the present invention may be incorporated with a wicking device for concentrating the aqueous fluid being tested in the area of the indicator system. Such a device usually comprises an absorbent wick having a substantially flat surface portion enclosed in a fluid impervious sheath having an aperture therein. The free available chlorine test reagent is incorporated with the flat surface portion of the wick exposed within the aperture in a manner such that when the aperture is immersed into the fluid being tested, the fluid contacts the test reagent as it flows into and is absorbed by the wick.

In its simplest form, a piece of bibulous filter paper of sufficient porosity and capillary affinity to cause the fluid being tested to migrate into the paper is coated or otherwise incorporated with the test reagent and the wick is enclosed in a fluid impervious sheath having an aperture in the area thereof overlying the portion of the paper incorporated with the test reagent. When the device is immersed into a fluid to be tested, the amount or volume of aqueous test fluid contacting the test reagent at the aperture is substantially more than would contact said reagent if the paper were immersed in the test fluid in unsheathed condition, and is dependent upon the capacity of the wick to absorb the test reagent. The net result of using such a device is that a substantially greater volume of the substance being detected is made available for contact with the test reagent than could be achieved by using a simple "dip and read" test device. Thus, lower concentrations of free available chlorine may be detected in the test fluid.

As used in the present specification, the following definitions of terms apply: test reagent is defined as a chemical composition or compound which is specifically reactable with free available chlorine and gives an observable or detectable response thereto; test fluid is defined as any aqueous medium to be assayed for the presence or absence of free available chlorine; wick is defined as means used to retain a test reagent and absorb a test fluid; sheath is defined as means used to enclose a wick and to direct a test fluid into and through the wick in a defined manner; aperture is defined as an opening in a sheath, preferably planar, which permits test fluid flow into a wick through the portion thereof exposed at said aperture, such that flow of the test fluid into the wick is channeled and controlled.

BRIEF DESCRIPTION OF THE DRAWINGS

In the accompanying drawings:

Referring now specifically to the drawings, FIGS. 1 and 2 represent a form of the invention wherein an elongated flat rectangular member 16 of plastic or other suitable material is formed with a rectangular offset well portion 12 at one end and with an integral handle portion 14. A wick 11 in the form of a square of bibulous paper is positioned in the well and secured therein by means of a piece of pressure sensitive cellulose or plastic adhesive tape 15 which completely covers wick 11, and with well portion 12, forms a sheath for said wick. An aperture 13 in member 16 is positioned in the center of the well portion 12 and its contiguous to the wick 11 which is impregnated throughout with a reagent.

FIGS. 3 and 4 represent a form of the invention wherein an elongated wick member 11a is laminated between two elongated strips 12a and 15a of plastic or other suitable material sealed, as by adhesive or heat sealing, along both side edges and one end edge to form a sheath for said wick. A test reagent is impregnated into the end portion of the wick 11a adjacent to the sealed end of the sheath, and an aperture 13a is formed in the strip 12a at the same end of the sheath.

In FIG. 5, the color response of various test reagents used in conjunction with the device shown in FIGS. 1 and 2 is demonstrated. Specifically Plot A represents the composition described in Example 1 of this specification and comprises a composition for determining free available chlorine using syringaldazine alone as the test reagent, while Plot B represents the composition described in Example 2 and comprises the use of a test reagent consisting of a combination of syringaldazine and vanillinazine. Plot C represents the color response achieved using the composition of Example 3, i.e., syringaldazine alone buffered to a pH of 6 with phosphate buffer. Plot D shows the color response of a combination of syringaldazine and vanillinazine buffered to a pH of 6 using phosphate buffer as described in Example 4. In each of these examples, increased color response is indicated by a greater meter deflection which is represented by the ordinate of the graph, while increasing free available chlorine concentration is represented along the abscissa.

Figure 1:
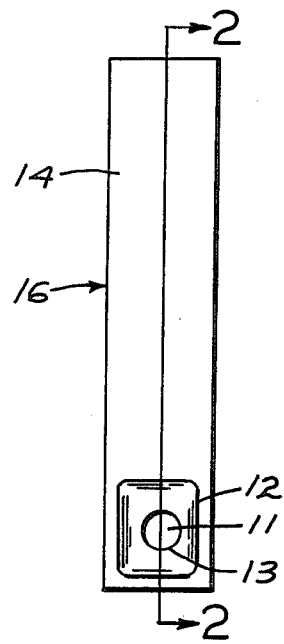
FIGS. 1 and 3 are front views of specific embodiments of test devices of the present invention.

The wick material used in the test devices of the present invention may be any of numerous absorbent materials both natural and synthetic. These substances are characterized by their ability to absorb a fluid by capillary attraction or affinity such that the fluid contacting the substance is drawn into the body or structure until the wick substance is saturated and is retained wherein. Those skilled in the art of using such substances often refer to these materials as bibulous, that is, having the ability to "drink" the fluid coming in contact therewith. Such substances include, inter alia, absorbent paper, such as filter paper, cloth, fibrous synthetic polymers, processed wool, certain clay-like substances, polymeric gels which have been processed to form membrane structures, and the like.

The sheaths of the test devices disclosed may be constructed of any of the numerous water impervious resinous film-forming materials such as, for example, polyethylene, polypropylene, polyvinyl chloride, polyvinyl acetate, polyamide, polyethylene terephthalate and various combinations thereof.

As far as the overall construction or physical structure of the present test device is concerned, a great number of variations may be made without departing from the scope or spirit of the inventive concept disclosed herein. Basically, the wick is enclosed in a sheath provided with aperture means of predetermined area through which the test fluid can flow. A test reagent is associated with the wick and with the sheath aperture in such a manner that the fluid being tested, on passing through the aperture, contacts the reagent in the area of the wick exposed at the aperture. As far as the reagent and wick are concerned, the reagent may simply be incorporated therewith such as, for example, by impregnation with a solution of the reagent, followed by drying. Alternatively, the reagent may be added as a separate entity to the wick such as by using a separate reagent-impregnated paper disc over the wick portion at the area of the sheath aperture. At any rate, the reagent need only be incorporated with the wick in the vicinity of the sheath aperture, since the fluid being tested must flow through this area and then, by capillary affinity, migrate into the body of the wick, causing additional test fluid to pass through the aperture and contact the reagent.

In regard to the structural relationship between the test reagent, sheath and aperture, the test reagent must be placed at the aperture of the sheath in such a manner that the test fluid must pass in contact with the reagent at the aperture in order to migrate into the body of the wick, and must not be able to flow into the wick without contact with the reagent.

It is preferable that at least one of the test device constitutents be reasonably rigid in order to facilitate handling of the test device. In this regard, the sheath may advantageously perform the function of adding rigidity to the test device since this constituent is generally polymeric in nature and may easily be made to have this rigidity characteristic. Moreover, the sheath is preferably elongated or otherwise provided with a handle portion to facilitate manipulation of the test device.

Although the test devices of the present invention may comprise a wide variety of shapes and sizes, a preferable physical embodiment or form is shown in FIG. 1 and involves the use of a square (15 × 15 mm.) of rather thick (about 1 mm.) bibulous paper as the wick 11. The dimensions of the strip 16 of fluid impervious, opaque plastic material are about 20 × 100 mm., and the aperture 13 preferably has a diameter of 5 mm. The wick 11 is incorporated with a test reagent.

The physical form of the present test device is not critical; however, the inter-relationship of the aperture size and the capacity of the wick to absorb fluid is important. In this connection, the volume of fluid contacting the test reagent depends on the size of the aperture and the fluid volume capacity of the wick. Such parameters may be easily adjusted to meet the needs of the specific test system and device being prepared. Generally speaking, in a test device in which the wick has a given volume capacity, as the aperture is made smaller, the ratio of fluid volume to reagent area exposed at the aperture is increased.

In use, the test devices of the present invention are simply dipped into the test fluid, held therein until the wick absorbs the desired amount of fluid or becomes saturated, and then withdrawn. The immersion period may be timed, or a chemical indicator may be combined with the wick to give a visual indication of saturation of the wick to the extent desired. This latter embodiment may simply and effectively comprise the utilization of a chemical which gives a visual response to the presence of the fluid being tested, such chemical being placed on the wick in the form of a transverse line or bar. This chemical may simply be anydrous cobalt chloride which changes color from blue to pink when contacted by the aqueous fluid migrating through the wick which change of color gives a signal that the device should be removed from the fluid being tested.

A more sophisticated and utilitarian signal system may be provided by placing a first line or bar of a colorless chemical across the width at an intermediate portion of the wick and a second colorless chemical bar across the wick at a position further away from the aperture, such that fluid moving along the wick dissolves the chemical in the first bar and carries it into the second bar. A visible chromogenic response results, indicating that the test device should be withdrawn from the fluid being tested. Examples of such first and second chemicals are potassium ferrocyanide and ferric ammonium sulfate respectively. Obviously the second bar is placed in a specific position on the wick providing the color reaction when the desired volume of fluid has passed through the aperture an contacted the reagent thereat. Moreover, any number of bars may be utilized in conjunction with the wick to permit absorption thereinto of predetermined volumes of several fluids.

A third and simpler alternative to the above comprises merely allowing the device to remain in the fluid being tested for a period of time in excess of that required to saturate the wick. The obvious drawback of doing this resides in the possibility of leaching the reagent from the device with resulting loss in sensitivity. This, of course, would only happen if the device is allowed to remain in the fluid for a period of time far in excess of that required to carry out a test.

Since the fluid being detected must contact the reagent at the aperture, fluid soluble reagents may be immobilized to prevent solution thereof. This immobilization may be accomplished by any of the known methods of insolublizing a reagent in a matrix. A simple expedient is to treat the reagent with a material such as starch. Another means of immobilizing the reagent involves treating or coating the reagent and matrix thereof with a semi-permeable membrane of polymeric material which affixes the reagent to the matrix. Other suitable means involve chemically or physically bonding the reagent to the wick or matrix, such as for example by using insoluble adsorbents or paper containing insoluble ion-exchange resins.

The following examples are merely descriptive of the present invention and are not intended to place any limitation thereon.

EXAMPLE 1

Figure 2:
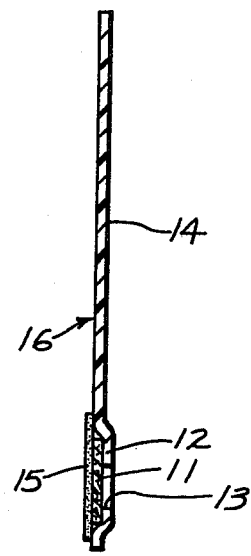
FIGS. 2 and 4 are longitudinal sectional views taken along the lines 2—2 and 4—4 respectively of FIGS. 1 and 3 respectively.
Figure 3:
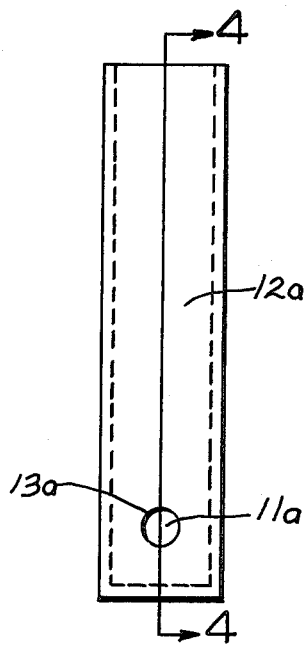
Figure 4:
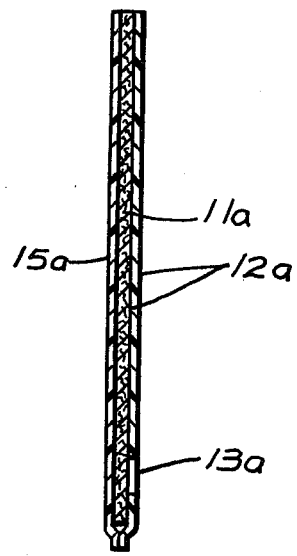

Sheets of Eaton-Dikeman No. 301 bibulous paper having a thickness of about 1.0 mm. were impreganted with a solution containing 0.05% (weight to volume) syringaldazine in 95% ethanol and dried for 20 minutes at 100° C. The dried sheets were cut into 15 × 15 mm. squares and each square used in a device of the type shown in FIGS. 1 and 2. The well portion 12 of the device was about 16 × 16 mm. and the aperture 13 thereof had a diameter of 5 mm.

Figure 5:
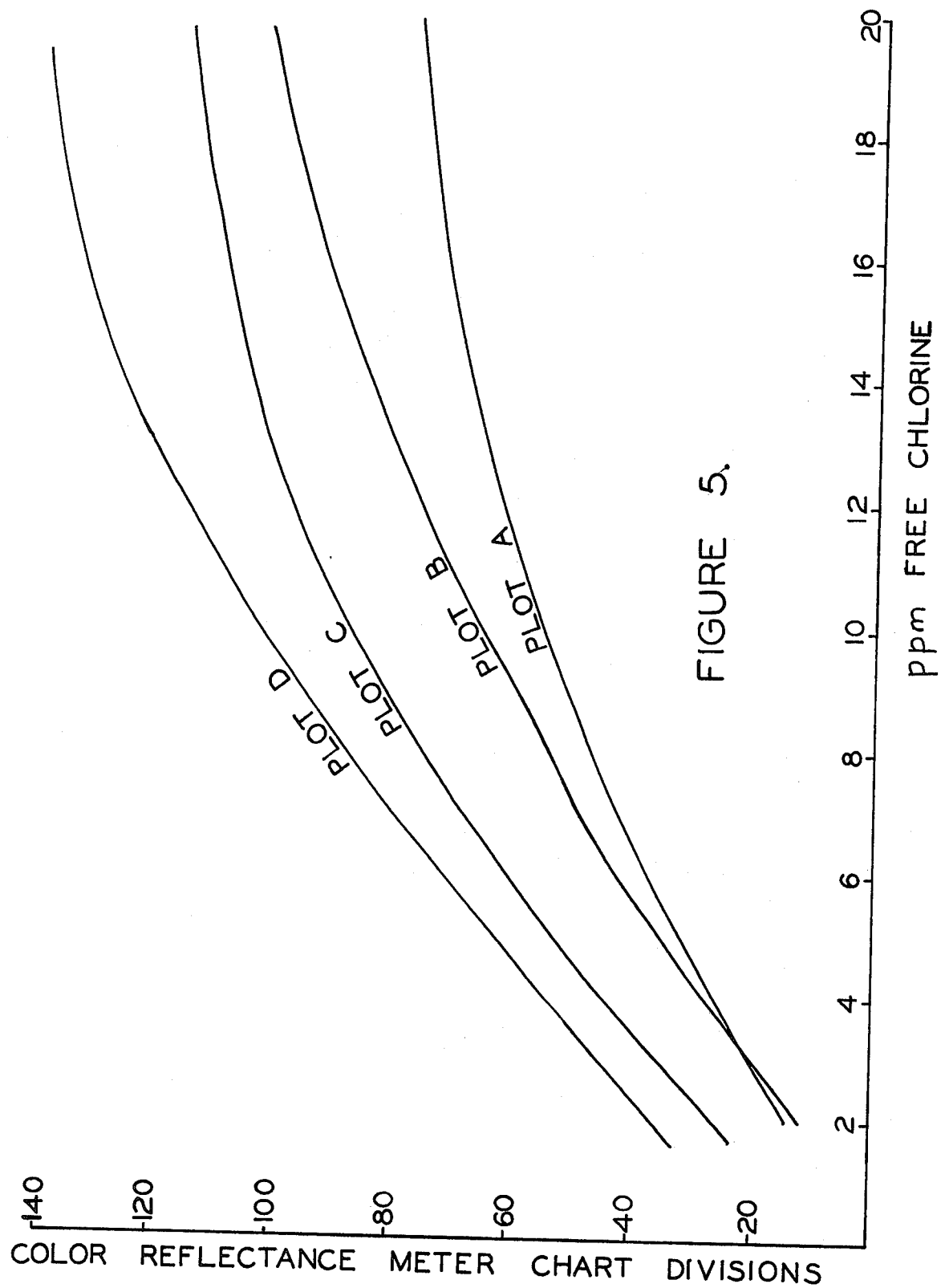
FIG. 5 is a chart showing color response achieved using the device shown in FIGS. 1 and 2 in combination with various test reagent systems.

Test devices so produced were then separately immersed for 10 seconds in water having concentrations of free available chlorine of 0.5 to 20 ppm. and withdrawn therefrom. The color of the test reagent area exposed at the aperture changed from yellow to varying intensities of purple depending upon the concentration of chlorine in the water. The color response of this composition is shown as Plot A of FIG. 5 wherein concentration of free chlorine in ppm was plotted against chart response obtained using a Joyce Chromoscan reflectance meter for measuring color response.

EXAMPLE 2

The procedure of Example 1 was repeated except that an impregnating solution comprising equal volumes of 0.1% (weight/volume) vanillinazine in 95% ethanol and 0.1% (weight/volume) syringaldazine in 95% ethanol was used in place of the 0.05% syringaldazine solution described therein. The increased color response of this composition represented by Plot B of FIG. 5 as compared to that obtained in Example 1 may be seen by comparing Plot A and Plot B.

EXAMPLE 3

The procedure of Example 1 was repeated except that an impregnating solution comprising equal volumes of 0.1% syringaldazine and 0.1M phosphate buffer having a pH of 6.0 replaced the impregnating solution described therein. The color response achieved using this test reagent system is shown as Plot C of FIG. 5. The increased color response due to the buffering action of the phosphate buffer can be seen by comparing this plot to Plots A and B.

EXAMPLE 4

The procedure of Example 2 was repeated except that 2 volumes of 0.1M phosphate buffer having a pH of 6.0 were added to the impregnating solution. The increased color response of this composition is shown as Plot D of FIG. 5.

EXAMPLE 5

This example shows the ability of the compositions and devices of the present invention to detect free available chlorine. A test device was prepared as described in Example 4 and shown in FIGS. 1 and 2. An aqueous solution containing 1 ppm free available chlorine was prepared and 1 ppm $(NH_4)_2CO_3$ added to a portion thereof in order to convert the free available chlorine to combined available chlorine in the form of a chloramine. These solutions were then tested for chlorine content using (1) the devices prepared as described in Example 4 and (2) the standard orthotolidine-arsenite method. This latter method is specifically designed to detect free available chlorine as well as total residual chlorine.

Specifically, the ortho-tolidine reagent was prepared by dissolving 1.35 grams of ortho-tolidine dihydrochloride in 500 mls. of distilled water and adding a mixture of 150 mls. of concentrated HCl in 350 mls. of distilled water to this solution. The sodium aresenite solution was prepared by dissolving 5.0 g. of $NaAsO_2$ in distilled water and diluting to 1 liter.

The chlorine containing samples were analyzed for free available chlorine and total residual chlorine by the following procedure:

1. Two separate 10 ml. comparator cells were labeled A and B respectively.
2. To cell A, was added 0.5 ml. of ortho-tolidine reagent, 10 ml. of water sample and 0.5 ml. of arsenite solution. This solution was imediately compared to color standards and the result recorded which represents free available chlorine.
3. To cell B was added 0.5 ml. of ortho-tolidine and 10 ml. of water sample. The result obtained by comparison to color standards after 5 minutes represents total residual chlorine. The following results were obtained from the above tests as well as tests using the devices of the present invention:

| Test Solution | Method of Present Invention Free Available Cl* | Ortho-tolidine-arsenite method | |
|---|---|---|---|
| | | Free Available Cl* | Total Residual Cl* |
| 1 ppm Chlorine | 1.0 | 0.9 | 0.9 |
| 1 ppm Chlorine plus 1 ppm $(NH_4)_2CO_3$ | 0 | 0.2 | 0.8 |

*concentrations in ppm

From the above results it was observed that the device prepared in Example 4 measured only free available chlorine whereas ortho-tolidine alone measured total residual chlorine. The latter yielded a much higher value which was not indicative of the disinfectent present in the water sample.

What is claimed is:

1. A method for detecting only free available chlorine in an aqueous fluid suspected of containing both free and combined available chlorine which comprises contacting the fluid with a test reagent comprising an indicator substance selected from the group consisting of (1) a compound having the formula

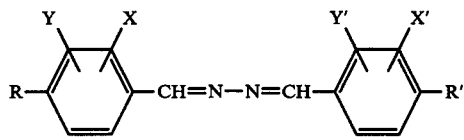

where R and R' are selected from the group consisting of hydroxy and amino groups and X, X', Y and Y' are selected from the group consisting of hydrogen, hydroxy, methyl and methoxy groups and (2) combinations thereof, and a buffer for adjusting the pH of the test reagent to about from 3.5 to 8.5; and comparing the color obtained with colors obtained using standard chlorine containing aqueous fluids.

2. A method as in claim 1 wherein the pH of the test reagent is 6.0.

3. A method as in claim 1 wherein the indicator substance comprises syringaldazine.

4. A method as in claim 1 wherein the indicator substance is a combination of syringaldazine and vanillinazine.

5. A method as in claim 1 wherein the test reagent is incorporated with a carrier member.

6. A method as in claim 5 wherein the carrier member is bibulous paper and the test reagent is impregnated into or onto said paper.

* * * * *